United States Patent [19]

Aulie

[11] Patent Number: 5,171,325

[45] Date of Patent: Dec. 15, 1992

[54] HINGE STRUCTURE FOR PROSTHETIC JOINT

[76] Inventor: Alan L. Aulie, 3615 Northwest Way, Redmond, Oreg. 97756

[21] Appl. No.: 779,649

[22] Filed: Oct. 21, 1991

[51] Int. Cl.⁵ .............................................. A61F 2/64
[52] U.S. Cl. ...................................... 623/43; 623/46; 623/39; 16/225; 16/277
[58] Field of Search ...................................... 623/39–46; 403/111, 145, 149; 16/225, 277

[56] References Cited

U.S. PATENT DOCUMENTS

| 21,289 | 8/1858 | Wilcox | 623/40 X |
|---|---|---|---|
| 336,904 | 3/1886 | Dunham | 623/46 X |
| 744,801 | 11/1903 | Rowley | 623/45 |
| 3,289,877 | 12/1966 | Wolf | 16/225 X |
| 3,820,169 | 6/1974 | Long et al. | |
| 4,064,569 | 12/1977 | Campbell | |
| 4,135,254 | 1/1979 | Weber et al. | 623/46 X |
| 4,145,766 | 3/1979 | May | |
| 4,206,519 | 6/1980 | Blatchford et al. | |
| 4,212,087 | 7/1980 | Mortensen | |
| 4,236,274 | 12/1980 | Omote et al. | 16/225 |
| 4,310,932 | 1/1982 | Nader et al. | |
| 4,911,709 | 3/1990 | Marlow et al. | 623/39 |
| 4,994,086 | 2/1991 | Edwards | 623/26 |
| 4,997,449 | 3/1991 | Prahl et al. | 623/44 |

FOREIGN PATENT DOCUMENTS

| 3033817 | 4/1982 | Fed. Rep. of Germany | 16/277 |
|---|---|---|---|
| 0441822 | 10/1949 | Italy | 623/39 |
| 0358545 | 1/1962 | Switzerland | 623/39 |

OTHER PUBLICATIONS

Klopsteg et al., *Human Limbs and Their Substitutes*, McGraw-Hill, 1954, pp. 525–528.

Primary Examiner—Randall L. Green
Assistant Examiner—D. Willse
Attorney, Agent, or Firm—John F. Ingman

[57] ABSTRACT

A prosthetic joint includes an anterior linking and support member and a posterior linking and support member, formed of a resilient material, which act as cantilever flat springs to provide an intrinsic extension bias while furnishing the rigid structure necessary to support the axial loads and extension moments induced by the amputee. A prosthetic knee joint includes a base formed of a resilient polyamide such as nylon 6/6, from which an anterior linking and support member, generally of an L-shape, and a posterior linking and support member, monolithically extend upwards. Formed to provide the inherent stability of four-bar linkage, these resilient linking and support members are pivotally attached to a yoke member to act as cantilever single-leaf flat springs which provide an intrinsic extension moment to the prosthetic knee joint which may vary according to the amount of flexion of the knee joint. The extension moment of the knee joint is translated into compression at the anterior linking and support member and tension at the posterior linking and support member, thereby allowing the use of a relatively low-strength resilient material in the knee joint construction. A common double-acting hydraulic damper is used to reduce the swing rate of the knee joint, permitting a desired gait and reducing terminal impact at full extension.

11 Claims, 2 Drawing Sheets

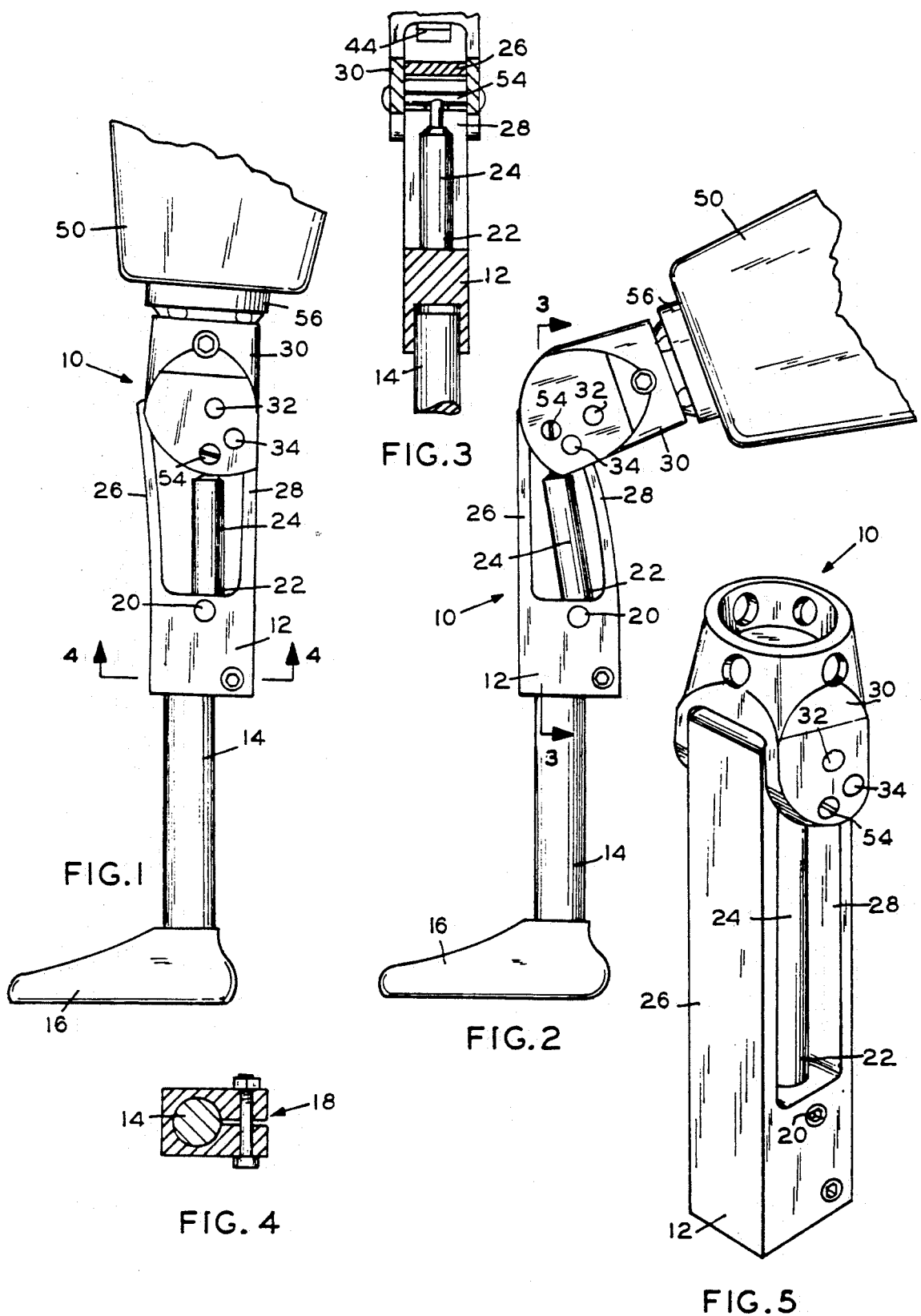

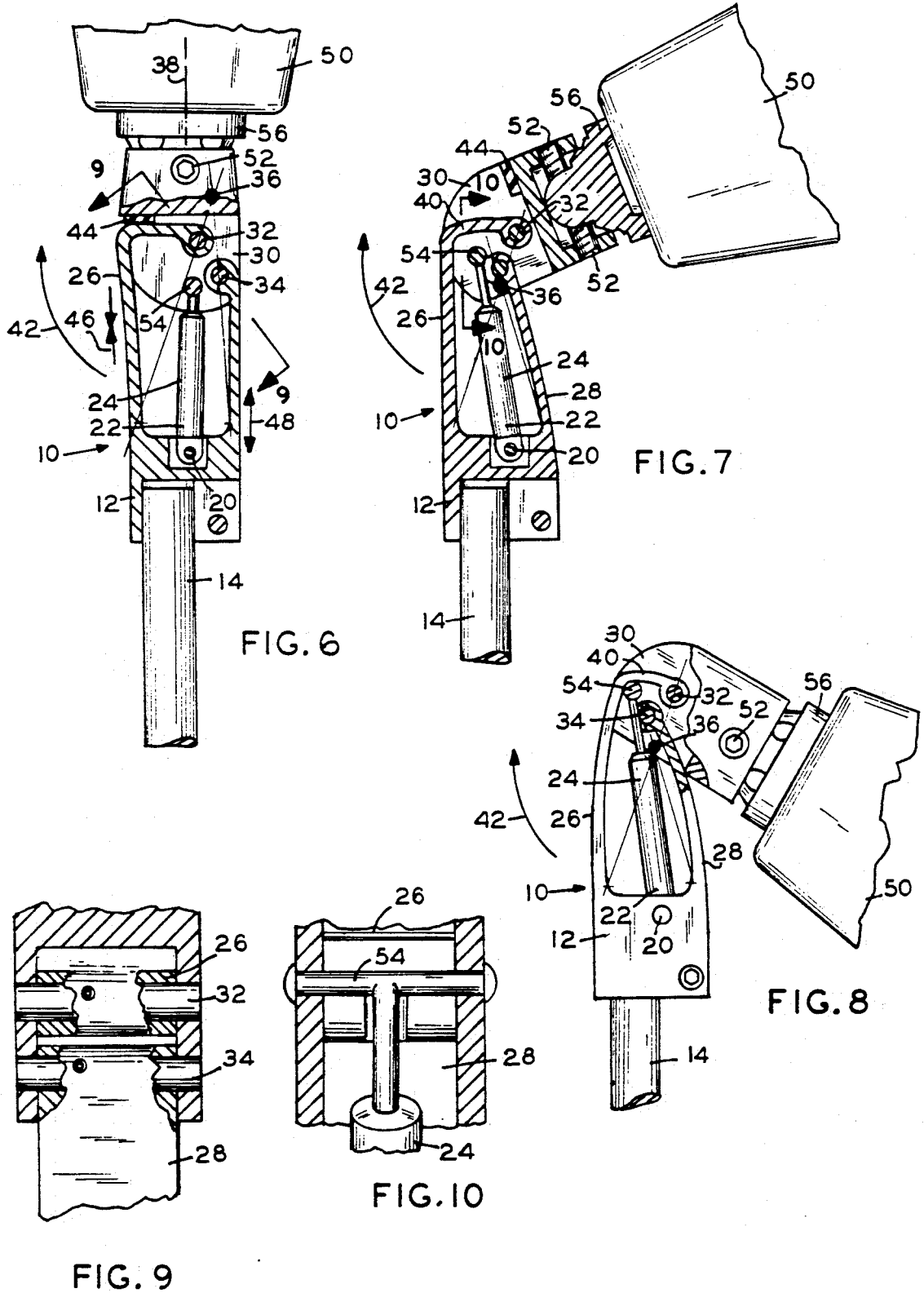

HINGE STRUCTURE FOR PROSTHETIC JOINT

BACKGROUND OF THE INVENTION

1. Field of the Invention

The invention involves a prosthetic joint for use by amputees, and, more particularly, a prosthetic joint utilizing polymeric linkage which provides intrinsic extension bias, as exemplified by a prosthetic knee joint.

2. Description of the Prior Art

Various knee joints have been designed for use by above-knee amputees. Recent designs have included four-bar linkage which provides a high center of rotation and inherent stability. However, these knee joints generally have been complicated in structure, including complex spring and/or hydraulic mechanisms to achieve the desired performance, which has resulted in high cost, heavy weight, and inadequate reliability.

What is needed is a prosthetic joint which provides an intrinsic extension assist, and is lightweight, noise free, simple in structure, reliable in operation and relatively inexpensive.

SUMMARY OF THE INVENTION

The present invention involves a prosthetic joint for amputees which is formed to meet the aforementioned needs. A polycentric joint, includes an anterior linking and support member and a posterior linking and support member, formed of a resilient material, which act as cantilever flat springs to provide an intrinsic extension bias while providing the rigid structure necessary to support the axial loads and extension moments induced by the amputee.

Accordingly, in a preferred embodiment, a prosthetic knee joint, includes a base formed of a resilient polyamide such as nylon 6/6, from which an anterior linking and support member, generally of an L-shape, and a posterior linking and support member, monolithically extend upwards. Formed to provide the inherent stability of four-bar linkage, these resilient linking and support members are pivotally attached to a yoke member to act as cantilever single-leaf flat springs which provide an intrinisc extension moment to the prosthetic knee joint which may vary according to the amount of flexion of the knee joint. The extension moment of the knee joint is translated into compression at the anterior linking and support member and tension at the posterior linking and support member, thereby allowing the use of a relatively low-strength resilient material in the knee joint construction. A common double-acting hydraulic damper is used to reduce the swing rate of the knee joint, permitting a desired gait and reducing terminal impact at full extension.

BRIEF DESCRIPTION OF THE DRAWINGS

FIG. 1 illustrates a side elevational view of an artificial leg which includes the prosthetic knee joint in extension.

FIG. 2 illustrates a side elevational view with the prosthetic knee joint at approximately 45-degrees flexion.

FIG. 3 illustrates a cross section view of the prosthetic knee joint as seen at line 3—3 of FIG. 2.

FIG. 4 illustrates a cross section view of the shank clamp as seen at line 4—4 of FIG. 1.

FIG. 5 illustrates a perspective view of the prosthetic knee joint in extension.

FIG. 6 illustrates a cross section side view of the prosthetic knee joint in extension.

FIG. 7 illustrates a cross section side view of the prosthetic knee joint at approximately 45-degrees flexion.

FIG. 8 illustrates a cross section side view of the prosthetic knee joint at approximately 120-degrees flexion.

FIG. 9 illustrates a cross section view as seen at line 9—9 of FIG. 6.

FIG. 10 illustrates a cross section view as seen at line 10—10 of FIG. 7.

DESCRIPTION OF THE PREFERRED EMBODIMENT

The prosthetic joint may be used in various prosthetic limb applications, which include and are exemplified by the prosthetic knee joint subsequently described.

Turning now to the drawings, the prosthetic knee joint 10 is shown in FIG. 1 in extension and in FIG. 2 at approximately 45-degrees flexion. FIGS. 6, 7, and 8 provide cross sectional views in extension, at 45-degrees flexion, and at 120-degrees flexion, respectively.

The prosthetic knee joint 10 generally is constructed, as described below, of a lightweight resilient material, using the elastic properties of the material to provide intrinsic bias to extension while utilizing the same material in compression and tension to provide the rigid structure necessary to support the loads induced by the amputee during ambulation. The preferred material is an unfilled polyamide commonly known as nylon 6/6.

In the preferred embodiment, the prosthetic knee joint 10 includes a machined rigid base 12 which provides for mounting of a tubular shank 14 which extends to a prosthetic foot 16. A shank clamp 18, such as seen at FIG. 4, holds the shank 14 in position. The base 12 also mounts, using pin 20, the lower end 22 of a hydraulic damper 24, as discussed subsequently. Extending upwards, preferably monolithically, from the base 12 are an anterior linking and support member 26 and a posterior linking and support member 28 which act both as columns to support axial loads of body weight and as a flexible, resilient linkage between the base 12 and the yoke 30. Two pivots 32 and 34 connect the yoke 30, through the anterior linking and support member 26 and the posterior linking and support member 28, respectively, to the base 12.

Amputee gait requires that a prosthetic knee joint 10 be over-stabilized when in extension to avoid accidental buckling of the knee joint 10. The anterior and posterior vertical support members 26 and 28 act as resilient links, the pivots 32 and 34 being located upon the yoke 30 so that, when in extension, as seen in FIG. 6, the instant center of rotation 36 is posterior to the axial line of weight bearing 38. This instant center of rotation 36 also is located above the pivots 32 and 34, reducing the force required to initiate flexion. Upon flexion, as seen in FIGS. 7 and 8, the instant center of rotation 36 moves to a lower position thereby shortening the effective length of the shank 14 when the shank 14 is swinging, thereby reducing stumbling. While the present structure is significantly different, this resulting movement of the instant center of rotation 36 is common to many four-bar linkage knees currently available, as will be recognized by a person familiar with the art, and it not described further here.

The anterior and posterior linking and support members 26 and 28 are formed, preferably machined, as illustrated, with the anterior linking and support member 26 being sharply curved to proximate an "L"-shape. The "L"-shape of the anterior linking and support member 26 allows a yoke 30 to rotate or pivot whereat the posterior linking and support member 28 and its pivot 34 passes beneath the upper leg 40 of the anterior linking and support member 26 and its pivot 32, thereby avoiding any need for cross-linking and the consequential need for a strength reducing split of either anterior or posterior linking and support member 26, 28. The arrangement of the resilient anterior and posterior linking and support members 26 and 28 permits the action of four-bar linkage, with its relocation of the instant center of rotation 36, while providing axial load supporting strength and rigidity by the support members 26 and 28. The anterior and posterior linking and support members 26 and 28 act as cooperative cantilever single-leaf flat springs thereby imparting, when in flexion, an extension moment 42 to the knee joint 10 as can be seen in the bending of the resilient linking and support members 26 and 28 in FIGS. 7 and 8. As will be recognized by those skilled in the art, the extension moment 42 preferably increases from full extension (FIG. 6) to about 45-degrees of flexion as seen in FIG. 7, then decreases due to the relative positioning of the pivots 32 and 34 as the base 12 rotates to 120-degrees, as seen in FIG. 8. This reduction in extension moment 42 importantly allows the prosthetic knee joint 10 to stay flexed and provide a natural appearance when the amputee is seated. The amount of flexion may be limited to approximately 120-degrees by interference between the yoke 30, the anterior linking and support member 26, and the posterior linking and support member 28. When the prosthetic knee joint 10 is in extension, further forward rotation is limited by an extension stop 44, preferably formed as an elastomeric bumper, which is attached to the yoke 30, engaging the upper leg 40 of the anterior linking and support member 26. The elastomeric extension stop 44 may, of course, also be attached at a comparable engaging position (not shown) on the upper leg 40 of the anterior linking and support member 26.

The combined loading of, for example, a 250 lbs. load along the axial line of weight bearing 38, and a 100 lb-ft extension moment 42 is withstood by the relatively low strength resilient materials in the prosthetic knee joint 10 by virtue of the design. In extension, the axial load is directly supported by the anterior and posterior linking and support members 26 and 28 in compression while the extension moment 42 is translated into compression 46 on the anterior linking and support member 26 and tension 48 on the posterior linking and support member 28. The effect of fatigue is conventionally reduced by varying the anterior and posterior linking and support members 26 and 28 in thickness, width and length so that the members 26 and 28 bend about large radii with low stress levels produced in the members 26 and 28.

The yoke 30 additionally provides means to mount the stump socket 50 to the prosthetic knee joint 10. Attachment of the prosthetic knee joint 10 to the stump socket 50 may utilize a mounting member 56 with alignment being obtained by the adjustment of set screws 52. The preferred resilient material, nylon 6/6, provides a low-friction bearing surface about the pivots 32 and 34 which ensures provide smooth operation and low noise.

Without some means of control, the intrinsic extension moment 42 of the prosthetic knee joint 10 would swing the shank 14 rapidly forward, with a terminal impact at the extension stop 44. The action of the amputee's residual limb also tends to flex the knee joint 10 rapidly. To counteract these tendencies, a double-acting hydraulic damper 24 is fitted and connected between the base 12 at pin 20 and the yoke 30 at pin 54. The hydraulic damper 24 may be of conventional design, and should reduce the swing rate of the shank 14 sufficiently to provide a good gait, such as a rate of about 180-degrees per second. Other damping means such as pneumatic or friction also could be used.

While, in the preferred embodiment, the anterior and posterior linking and support members 26 and 28 are machined as monolithic extensions of a base 12 which is formed of nylon 6/6, the support members 26 and 28 also may be formed of other resilient materials which are appropriately fixed to a base 12. Other elements of the design could also be constructed of alternative materials, to include metals, other plastics and composites. However, the desired functioning, low weight, corrosion resistance, low part count and reduced manufacturing costs are important factors in the selection of the materials. Similarly, the major components (12, 26, 28, 30) are preferably machined but could be molded, cast or extruded.

Variants of the prosthetic knee joint 10 could be used for other prosthesis applications, such as the elbow, shoulder or hip.

A foam cover (not shown) would generally be used to cover the prosthetic knee joint 10 for cosmetic appearance.

It is thought that the prosthetic joint of the present invention and its many attendant advantages will be understood from the foregoing description and that it will be apparent that various changes may be made in form, construction and arrangement of the parts thereof without departing from the spirit and scope of the invention or sacrificing all of its material advantages, the forms hereinbefore stated being merely exemplary embodiments thereof.

I claim:

1. A prosthetic joint, comprising:
   a. a base member, having an anterior side and a posterior side;
   b. a yoke member;
   c. an anterior linking and support member formed of a resilient material, and having a first end and a second end; said anterior linking and support member being formed to initially extend toward said yoke member, and subsequently bend to a first pivotal connection upon said yoke member; said anterior linking and support member being substantially "L"-shaped, having a first leg extending from said base member and a second leg connecting to said yoke member;
   d. a posterior linking and support member formed of a resilient material, and having a first end and a second end; said posterior linking and support member extending toward said yoke member to a second pivotal connection upon said yoke member;
   e. means for non-pivotally connecting the first end of said anterior linking and support member at said anterior side of said base member, and the first end of said posterior linking and support member at said posterior side of said base member;
   f. means for pivotally connecting said second end of sand anterior linking and support member and said second end of said posterior linking and support member to said yoke member;

g. said means for pivotally connecting said anterior linking and support member and said posterior linking and support member to said yoke member being formed and positioned so that said resilient anterior and posterior linking and support members act in combination as cantilever flat springs, imparting an intrinsic spring bias to the prosthetic joint;

h. said first pivotal connection being positioned upon said yoke member at a greater distance from the base member than said second pivotal connection.

2. The prosthetic joint, as recited in claim 1, wherein, with said prosthetic joint in an extended position, said second leg of said anterior linking and support member and said yoke member are formed to abut so as to limit further rotation of said base member.

3. The prosthetic joint, as recited in claim 2, where an elastomeric bumper member is positioned between said second leg of said anterior linking and support member and said yoke member to lessen a terminal impact upon reaching said extended position.

4. The prosthetic joint, as recited in claim 1, wherein, additionally, a damping member is positioned between said base member and said yoke member to provide a damping effect on relative pivotal movement between said base member and said yoke member.

5. The prosthetic joint, as recited in claim 1, where said anterior linking and support member and said posterior linking and support member are monolithically formed with said base member.

6. The prosthetic joint, as recited in claim 1, where the resilient material of said anterior linking and support member and said posterior linking and support member is an unfilled polyamide.

7. A prosthetic knee joint, for above-knee amputees, comprising:

a. a base member, including means for connecting to a shank, and having a front side and a rear side;

b. a yoke member, including means for connecting to a stump socket;

c. an anterior linking and support member formed of a resilient material, and having an upper end and a lower end;

d. a posterior linking and support member formed of a resilient material, and having an upper end and a lower end;

e. means for non-pivotally connecting the lower end of said anterior linking and support member and the lower end of said posterior linking and support member to said base member so as to extend upwardly, in spaced relationship, from said base member;

f. means for pivotally connecting said upper end of said anterior linking and support member and said posterior linking and support member to said yoke member;

g. said anterior linking and support member being formed to initially extend substantially vertically from said front side of said base member, and subsequently bend rearward to a first pivotal connection upon said yoke member; said anterior linking and support member being substantially "L"-shaped, having a first leg extending from said base member and a second leg extending to said first pivotal connection upon said yoke member;

h. said posterior linking and support member extending substantially vertically from said rear side of said base member to a second pivotal connection upon said yoke member;

i. said first pivotal connection being positioned upon said yoke above said second pivotal connection;

j. said first pivotal connection and said second pivotal connection being positioned on said yoke member so that said resilient anterior linking and support member and said resilient posterior linking and support member act in combination as cantilever flat springs, imparting to the prosthetic knee joint in intrinsic spring bias to a straight extended position.

8. The prosthetic knee joint, as recited in claim 7, which additionally includes a damping member positioned between said base member and said yoke member to provide a damping effect on relative pivotal movement between said base member and said yoke member.

9. The prosthetic knee joint, as recited in claim 7, wherein, with said prosthetic knee joint is an extended position, said second leg of said anterior linking and support member and said yoke member are formed to abut so as to limit further rotation of said base member.

10. The prosthetic knee joint, as recited in claim 9, where an elastomeric bumper member is positioned between said second leg of said anterior linking and support member and said yoke member so as to lessen a terminal impact upon reaching said extended position.

11. The prosthetic knee joint, as recited in claim 7, where said anterior linking and support member and said posterior linking and support member are monolithically formed with said base member.

* * * * *